United States Patent [19]

Hench et al.

[11] Patent Number: 4,775,646
[45] Date of Patent: Oct. 4, 1988

[54] FLUORIDE-CONTAINING BIOGLASS TM COMPOSITIONS

[75] Inventors: Larry L. Hench; Derek B. Spilman; June W. Hench, all of Gainesville, Fla.

[73] Assignee: University of Florida, Gainesville, Fla.

[21] Appl. No.: 906,619

[22] Filed: Sep. 10, 1986

Related U.S. Application Data

[63] Continuation of Ser. No. 604,704, Apr. 27, 1984, abandoned.

[51] Int. Cl.$^4$ .............................................. C03C 10/00
[52] U.S. Cl. ........................................ 501/2; 501/1; 501/57; 623/16; 128/92 R; 428/432
[58] Field of Search ............... 501/2, 57, 72; 3/1.9; 128/92 C; 428/432–434; 623/16

[56] References Cited

U.S. PATENT DOCUMENTS

| | | | |
|---|---|---|---|
| 3,922,155 | 11/1975 | Broemer et al. | 501/57 |
| 3,981,736 | 9/1976 | Broemer et al. | 3/1.9 X |
| 4,103,002 | 7/1978 | Hench et al. | 428/432 X |
| 4,159,358 | 6/1979 | Hench et al. | 3/1.9 X |
| 4,234,972 | 11/1980 | Hench et al. | 3/1.9 |

FOREIGN PATENT DOCUMENTS 2378733  9/1978  France .................................. 3/1.9

OTHER PUBLICATIONS

Hench et al., J. Biomedical Material Res. Symposium, No. 4, pp. 25–42 (1973).

*Primary Examiner*—Steven Capella
*Attorney, Agent, or Firm*—Fleit, Jacobson, Cohn & Price

[57] ABSTRACT

A fluoride-containing bioactive glass composition suitable for bulk implant prosthetic devices and coatings for prosthetic devices, the bioactive glass compositions selected from glass formulations containing, by mole 46.1% $SiO_2$, 2.6% $P_2O_5$, 26.9% CaO and 24.4% $Na_2O$ and glass formulations containing, by mole, 52.1% $SiO_2$, 23.8% CaO, 21.5% $Na_2O$, 2.6% $P_2O_5$ wherein, respectively, 30 to 50 molar percent and 40 to 60 molar percent of the CaO is substituted with $CaF_2$. These fluoride-containing bioactive glass materials demonstrate high resistance to demineralization in physiological fluids as well as extensive apatite formation which shows a predominance of crystalline apatite of mixed phase character.

7 Claims, 10 Drawing Sheets

Apatite Formation
—vs.—
Fluorine Content

SUBSTITUTION OF 40% CaF, ±10% FOR CaO IN 45S5 BIOGLASS™

FIG. 1

REL. EXTENT OF APATITE FORMATION

OPTIMAL RANGE

WITHIN THE OPTIMAL RANGE THE BIOGLASS™ COMPOSITIONS EXIBIT:

1) EXTENSIVE APATITE FORMATION IN SURFACE REACTION FILMS;

WHICH

FIG. 2

REL. EXTENT OF CRYSTALLINITY

2) SHOW SIGNIFICANT PRESENCE OF CRYSTALLINE APATITE;

AND

FIG. 3

REL. PREDOMINANCE OF APATITE PHASES

3) A PREDOMINANCE OF MIXED APATITE PHASES

AND

FIG. 4

REL. RESISTANCE TO DEMINERALIZATION

% CaF$_2$ SUBSTITUTION

4) RESISTANCE TO BREAKDOWN BY DEMINERALIZING SOLUTION.

SUBSTITUTION OF 50% CaF, ±10% FOR CaO IN 52S4.6 BIOGLASS™

FIG. 5 — REL. EXTENT OF APATITE FORMATION vs % CaF₂ SUBSTITUTION (OPTIMAL RANGE)

FIG. 6 — REL. EXTENT OF CRYSTALLINITY

FIG. 7 — REL. PREDOMINANCE OF APATITE PHASES (MIXED / UNMIXED)

FIG. 8 — REL. RESISTANCE TO DEMINERALIZATION

% CaF$_2$ SUBSTITUTION

WITHIN THE OPTIMAL RANGE THE BIOGLASS™ COMPOSITIONS EXIBIT:

1) EXTENSIVE APATITE FORMATION IN SURFACE REACTION FILMS;

WHICH

2) SHOW SIGNIFICANT PRESENCE OF CRYSTALLINE APATITE;

AND

3) A PREDOMINANCE OF MIXED APATITE PHASES

AND

4) RESISTANCE TO BREAKDOWN BY DEMINERALIZING SOLUTION

Na Leach Rates -vs- Time for
45S5 Flouride Series Glasses

FIG. 9

Na Leach Rates -vs- $CaF_2$ Substitution
for 45S5 Base Composition

Summary

FIG. 17

FLUORIDE-CONTAINING BIOGLASS ™ COMPOSITIONS

This application is a continuation, of application Ser. No. 604,704, filed 4/27/84 abandoned.

BACKGROUND OF THE INVENTION

1. Field of the Invention

The present invention relates generally to fluoride-containing bioactive glass compositions of highly specific compositional ranges having substantially improved resistance to demineralization which also demonstrate the capability of forming an extensive layer of crystallized mixed apatite (carbonate-fluorohydroxylapatite) phases when exposed to physiological solutions. The fluoride-containing bioactive glass compositions of the instant invention are useful as prosthetic implants or implant coatings in dental and surgical applications where optimization of durable chemical bonding with living tissue is desirable.

2. Brief Description of the Prior Art

Bioglass ™ 45S5 is a bioactive glass containing 46.1% $SiO_2$, 2.6% $P_2O_5$, 26.9% CaO and 24.4% $Na_2O$, all percents being mole percents, and was developed to promote the formation of direct chemical bonding at the interface between mammalian bone and the glass, the direct bond obtained without the requirement for a porous structure. The advantages of the nonporous structure are, among others, that the intrinsic high strength of the material is retained and that the glass is useful as a coating for high strength materials such as stainless steel or aluminum oxide.

In an article entitled "Direct Chemical Bonding Between Bioactive Glass-Ceramic Materials and Bone" by Hench et al, Journal of Biomedical Materials Research Symposium, No. 4 (1973), pages 25–42, experimental work was reported on a single glass composition wherein 50 molar % of the CaO of the 45S5 glass was replaced with $CaF_2$. This bioactive glass containing 46.1% $SiO_2$, 2.6% $P_2O_5$, 13.45% CaO, 13.45% $CaF_2$ and 24.4% $Na_2O$, all percents being mole percents, is designated Bioglass ™ 45S5F and initially seemed to demonstrate increased resistance to aqueous attack and increased rate of apatite film formation as compared to the non-fluoride containing bioactive glass formulation.

However, in-vivo bone bonding studies of the 45S5F glass in the mid femur of mature rats indicated that bone bonding did not occur. This work is reported in a Greenlee, Jr. et al article published in the Journal of Biomedical Materials Research, 6 (1972), pages 235–244. Based on this work, it was concluded that the fluoride-containing bioactive glass has a much lower surface reactivity than the non-fluoride containing counterpart, this decreased surface reactivity making the glass unsuited for many implant applications.

A companion intramuscular implant study, the results of which were reported in the Hench et al article supra, pages 32–36, indicated that the cellular response to the 45S5F glass is fibroblastic in nature with the formation of elongated fibroblasts and large intercellular mature collagen fibers. Additionally, adjacent to the implant there was formed a row of large ovoid cells with single nuclei and foamy cytoplasm which were tightly adhered to the implant. The implant was stable and there was no adverse tissue reaction.

Stanley et al, Oral Surgery, Oral Medicine, Oral Pathology, 42(3) (1976), pages 339–356, "The Implantation of Natural Tooth Form Bioglass in Baboons", showed that the 45S5F glass used as dental implants in-vivo in baboon demonstrated a bonding ability equal to, but no better than, the 45S5 glass, with histopathological findings suggesting certain advantages residing in the 45S5F glass as compared to the 45S5 glass.

U.S. Pat. Nos. 4,159,358 and 4,234,972 to Hench & Buscemi disclose the 45S5 and 45S5F bioactive glass as bioactive coatings for prostheses comprising a metal substrate. Only the specific 45S5F bioactive glass containing 13.45 mole percent calcium fluoride is disclosed, the patents containing no suggestion that other fluoride contents might be useful. And while the references teach the 45S5F glass to be "extremely strong and resistant to body fluids", the references equate the 45S5 and 45S5F glasses.

U.S. Pat. No. 4,189,325 to Barrett et al discloses a large number of glass-ceramics for use in dental restoration work. The disclosed and claimed glasses contain 25 to 33 mole percent of $Li_2O_3$, 52 to 73.5 mole percent $SiO_2$, 0.5 to 5 mole percent $Al_2O_3$ and 1 to 10 mole percent CaO. However, the patent contains no reference to calcium fluoride as an additive and nothing to lead one with ordinary skill to make such a substitution.

U.S. Pat. No. 4,171,544 to Hench et al discloses compositions having, or capable of developing, a high specific area, porous, silica-rich surface capable of forming strong bonds with bone tissue. Highly porous glass and glass-ceramic compositions are disclosed, said compositions containing at least 80 weight percent $SiO_2$, hardened inorganic cements, and known biologically active glasses and glass ceramics. The high area silica-rich surface was thought to provide a large number of reactive sites for deposition and interaction of various of the organic and inorganic components of healing bone. However, the highly porous nature of the glass has a practical lack of utility because it cannot develop the requisite strength.

Thus a need has continued to exist for bioactive glass compositions which have sufficient resistance to demineralization in physiological fluids and sufficiently high proclivity for and rate of formation of mixed apatites in the reactive surface layer to provide a highly durable implant/tissue chemical bond to form with living tissue.

SUMMARY OF THE INVENTION

It is an object of the present invention to provide an improved bioactive glass composition.

It is a further object of the present invention to provide an improved bioactive glass composition suitable as a coating for high strength bulk implant prosthetic devices.

It is a still further object of the present invention to provide an improved bioactive glass composition suitable as bulk implant prosthetic devices.

It is yet another object of the present invention to provide an improved bioactive glass composition demonstrating a high surface reactivity rate in physiological solutions.

It is yet another object of the present invention to provide an improved bioactive glass composition demonstrating a high resistance to demineralization in physiological solutions.

It is a still further object of the present invention to provide a nonporous bioactive glass composition capable of forming soft and/or hard tissue chemical bonding with living tissue in a physiological environment.

These and other objects as will hereinafter become more apparent result from compositions comprising a bioactive glass selected from the glass having a composition consisting of 46.1% $SiO_2$, 2.6% $P_2O_5$, 26.9% CaO and 24.4% $Na_2O$ (Bioglass TM 45S5) and further wherein 30 to 50 molar % of the CaO is substituted with $CaF_2$, and a glass (Bioglass TM 52S4.6) having a composition consisting of 52.1 mol % $SiO_2$, 23.8 mol % CaO, 21.5 mol % $Na_2O$, 2.6 mol % $P_2O_5$ and further wherein 40 to 60 molar % of the CaO is substituted with $CaF_2$.

Applicants have discovered that the $CaF_2$-substituted compositions of the preceding paragraph demonstrate a substantially improved resistance to demineralization as compared to their non-$CaF_2$ substituted counterparts, and additionally demonstrate sufficient apatite formation, coupled with significant increases in the relative extent of crystallinity and relative predominance of mixed apatite phases to provide surprising and unexpected soft and/or hard tissue chemical bonding between prosthetic implants consisting of or coated with the invention compositions and the adjacent living tissue. By optimizing $CaF_2$ content vis-a-vis relative extent of apatite formation, presence of crystalline apatite, predominance of mixed apatite phases, and resistance to breakdown due to demineralization, compositions have been developed which have great utility in the area of surgical and dental prosthetics.

DESCRIPTION OF THE PREFERRED EMBODIMENT

Two specific presently known bioactive glass materials were studied with regard to $CaF_2$ substitution for a part or all of the CaO contained therein. Bioglass TM 45S5, as mentioned above, contains by molar % 46.1% $SiO_2$, 2.6% $P_2O_5$, 26.9% CaO and 24.4% $Na_2O$, with a calcium to phosphorus molar ratio (Ca/P) of 5. Bioglass TM 52S4.6, as mentioned above, contains by mol % 52.1% $SiO_2$, 23.8% CaO, 21.5% $Na_2O$, 2.6% $P_2O_5$ and a calcium to phosphorus ratio (Ca/P) of 4.6.

These bioactive glasses, as well as their fluoride-containing counterparts which comprise the instant invention, are prepared by methods well known to the art. Typically, the various constituents, $SiO_2$, $P_2O_5$, CaO, $Na_2O$ and $CaF_2$, in powder form, are mixed in a suitable mixing device such as a rolling mill and then heated to a temperature sufficient to cause the particles to melt and coalesce. The melt is then held at a specific temperature above the liquidus, such as 1350° C., for a predetermined period, such as 24 hours, to allow complete homogenization of the glass components within the melt by thermally activated diffusion. The melt may subsequently be cast to form bulk devices, applied as a coating to other materials such as stainless steel or alumina, or processed into a fine powder or frit for other coating processes of other applications.

It has now been discovered that substitution of 30 to 50 molar percent of the CaO in the 45S5 glass with $CaF_2$ and 40 to 60 molar percent of the CaO in the 52S4.6 bioactive glass results in the formation of bioactive glass especially well-suited for use in prostheses, either as bulk implants or as coatings for stainless steel alloys, dense aluminum oxide and the like.

The organic solids in bone matrix are fibrous protein collagen (90–95%) and mucoproteins, sialoproteins, lipids and phospholipids (5–10%). During mineralization in the formation of bone, the minerals aggregate in the bone or cartilage matrix, initially in an amorphous or noncrystalline state, although this amorphous state may have crystals of hydroxyapatite dispersed therein. Over time, the crystalline phase of hydroxyapatite becomes predominant. Thus, in determining the suitability of various materials as prosthetic implants with the ability to chemically bond to the adjacent living tissue, one critical evaluation revolves about the rate of apatite formation of the bioactive material and the rate of crystallization of the thus formed apatites.

Another critical characteristic of materials to be used as prosthetic implants is their ability to resist degradation mechanisms, one of which is demineralization as a result of long-term exposure in the physiological environment.

It is also known that natural bone mineral is a mixed carbonate hydroxylapatite with the carbonate actually built into the crystal lattice, occupying sites normally taken by phosphate groups and perhaps hydroxyl groups as well. Thus, the inventors have concluded that a bioactive glass with good biological compatibility must also demonstrate an ability to enhance the formation of mixed apatites in the reactive surface layer.

As a further requirement, the proposed bioactive glass compositions must be nontoxic. While this seems obvious, it also represents a real limitation which excludes certain materials which might otherwise have seeming potential.

In arriving at the ultimate invention of this disclosure, work was undertaken to investigate the two above-described 45S5 and 52S4.6 glasses with 0, 25, 50 and 100% molar substitutions of the CaO with $CaF_2$. The results of these experiments are presented graphically in FIGS. 1-8, FIGS. 1-4 pertaining to the 45S5 glass and FIGS. 5-8 pertaining to the 52S4.6 glass. Data concerning in-vitro surface reactivity and resistance to demineralization was collected from a series of static leach tests in conjunction with chemical solution analysis and Fourier Transform IR Reflection surface analysis.

Figure 4:
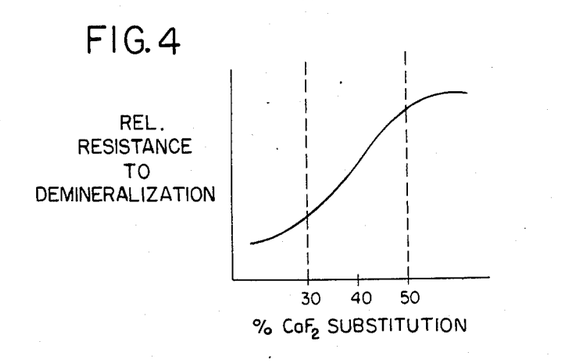
FIG. 4 is a graph showing the relationship between the relative resistance to demineralization (the y coordinate) and molar % substitution of CaO with $CaF_2$ (the x coordinate) for 45S5 glass.

In-vitro tests showed that the presence of $CaF_2$ in 50 or 100% molar substitution in the 45S5 glass significantly reduces the quantity of apatite formation (FIG. 1) while, at the same time, notably increasing the resistance to demineralization (FIG. 4). The 25% molar substitution of CaO with $CaF_2$ showed only a slight reduction in the quantity of apatite formed (FIG. 1) and a very significant increase in the crystalline character of the formed apatite (FIG. 2).

Subsequent X-ray diffraction analysis of the glass surface after 14 days exposure to Tris buffer solutions at 37° C. indicates a more crystalline nature of the 25% $CaF_2$ substituted 45S5 glass. The demineralization studies showed the 25% $CaF_2$ substituted glass to have increased resistance to demineralization as compared to the 45S5 glass with no substitution.

Figure 1:
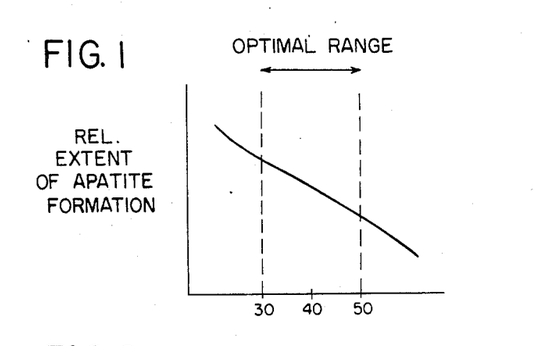
FIG. 1 is a graph showing the relationship between the relative extent of apatite formation (the y coordinate) and molar % substitution of CaO with $CaF_2$ (the x coordinate) for 45S5 glass.

In summary then, the results of the experimental work done on the 45S5 glass have demonstrated that while the extent of apatite formation decreases with a 40% or greater substitution of $CaF_2$ for CaO, sufficient apatite forms in the range of 30–50% $CaF_2$ substitution for the surface to remain bioactive (FIG. 1). The FIG. 1 data is based upon the ratio of infrared molecular stretching variations at the peak $1160-950$ cm$^{-1}$ which contains Si—O—Si bonds and Ca—O—P ($S_S$, $S_A$) bonds to the 630 cm$^{-1}$ peaks due to Ca—O—P molecular bonding vibrations ($R_A$).

Figure 2:
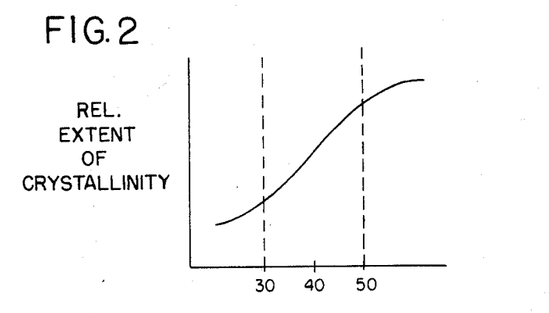
FIG. 2 is a graph showing the relationship between the relative extent of crystallinity of the apatite (the y coordinate) and molar % substitution of CaO with $CaF_2$ (the x coordinate) for 45S5 glass.

The experimental work has also demonstrated that the crystallinity of the surface reaction layer increases with the 40% or greater $CaF_2$ substitution (FIG. 2). Enhanced crystallization of the surface layer is highly desirable inasmuch as it also enhances bonding of collagen bone matrix and metabolic constituents at the implant interface. Evidence of FIG. 2 is based on the compositional dependence of loss of the amphorous base of X-ray diffraction spectra line and increased resolution of higher order lattice planes (202), (211), and (210) from 25% $CaF_2$ substitution onward.

Figure 3:
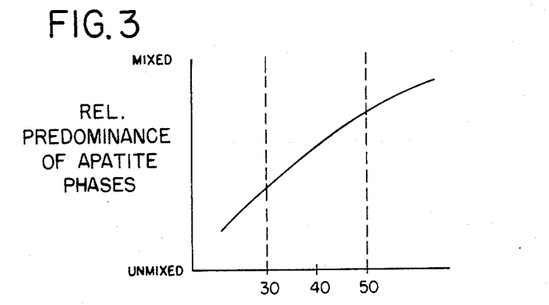
FIG. 3 is a graph showing the relationship between the relative predominance of apatite phases (unmixed to mixed along the y coordinate) and molar % substitution of CaO with $CaF_2$ (the x coordinate) for 45S5 glass.

Associated with increasing $CaF_2$ substitution is also a change in relative peak intensity of the (002)/(210) and the (002)/(211) X-ray peaks. The significance of this change is that the carbonate apatite or hydroxylapatite (002)/(210) peaks from X-ray analyses correspond more closely to the 0% and 25% substitutions whereas the composition of 40% or greater corresponds more closely to the mixed carbonate-hydroxyl-fluorapatites (dahllite). Thus the presence of critical concentrations of $CaF_2$ in the glass enhances the formation of mixed apatites in the reactive surface layer (FIG. 3).

The experimental work also demonstrated that resistance to demineralization increased proportionally to the percentage of $CaF_2$ substituted for CaO, reaching a plateau at approximately 50–60% substitution. This experimental work is depicted graphically in FIG. 4. The experimental data is a result of in-vitro exposures of the various glass formulation to a standard 10% formaldehyde, 30% formic acid demineralization fluid at 25° C.

Figure 5:
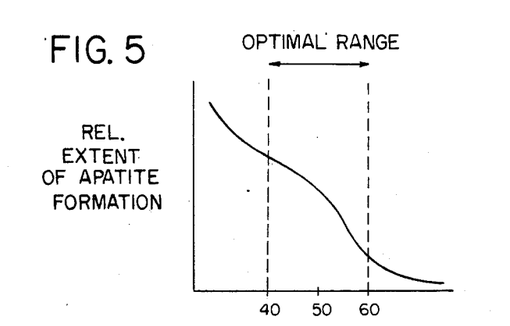
FIG. 5 is a graph showing the relationship between the relative extent of apatite formation (the y coordinate) and molar % substitution of CaO with $CaF_2$ (the x coordinate) for 52S4.6 glass.

The curves in FIGS. 1 and 5 are based on data collected by Fourier Transform IR Reflection Spectroscopy and Chemical Solution Analyses from a series of 1-, 3-, 7- and 14-day static leach tests performed in tris buffer at 37%. The curves of FIGS. 2, 3, 6, and 7 are based on X-ray diffraction studies of samples from the aforementioned experiments and comparisons of standard references from standard X-ray diffraction reference (JCPDS) files.

Figure 8:
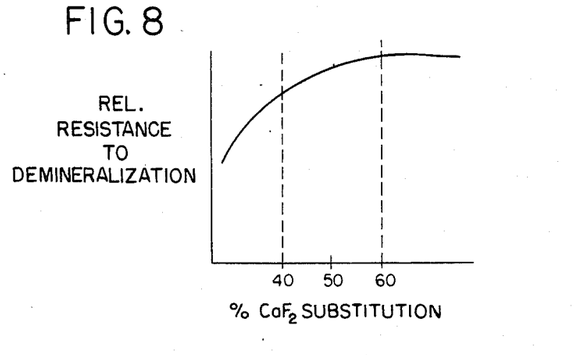
FIG. 8 is a graph showing the relationship between the relative resistance to demineralization (the y coordinate) and molar % substitution of CaO with $CaF_2$ (the x coordinate) for 52S4.6 glass.

The curves of FIGS. 4 and 8 are based on the size and number of particles remaining from each sample after a 24-hour exposure (at room temperature) to the demineralizing fluid and resulting relative extent of fragmentation of the samples.

From FIGS. 1–4, it may readily be seen that the optimum composition is a 45S5 with 30–50 molar % of the calcium oxide substituted by calcium fluoride. The glass remains bioactive while having significantly increased resistance to demineralization. Additionally, within this optimum range the glass also exhibits an enhanced extent of crystallization of the surface apatite layer formed and a greater mixture of hydroxylcarbonate and fluorapatites, thereby rendering the bioactive surface a distribution of phases more closely matching that of naturally mineralizing tissues.

With regard to the 52S4.6 glass, experimental work demonstrated that the extent of apatite formation decreases above a 60 molar % substitution of $CaF_2$ for CaO (FIG. 5). The evidence supporting this data is based on the emergence of characteristic apatite features in the 1600–400 cm$^{-1}$ region of IR reflection spectra of the various glass formulations exposed to Tris buffer at 37° C. for 14 days.

Figure 6:
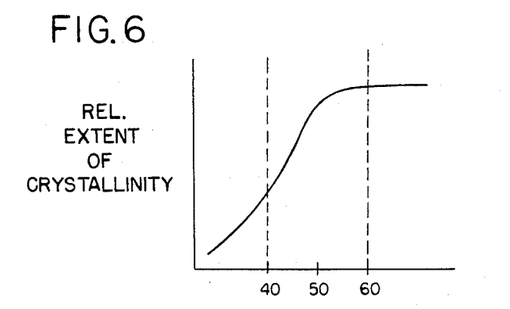
FIG. 6 is a graph showing the relationship between the relative extent of crystallinity of the apatite (the y coordinate) and molar % substitution of CaO with $CaF_2$ (the x coordinate) for 52S4.6 glass.

At the same time, crystallinity of the surface reaction film increases with 50% or greater $CaF_2$ substitution, the enhanced crystallization of the surface layer is desirable because it promotes bonding of collagen matrix and metabolic constituents at the implant interface (FIG. 6). This evidence is based on the compositional loss of the amorphous base line of the X-ray diffraction spectra between 25% and 50% substitution of $CaF_2$ and increased resolution of higher order peaks (202), (211), and (210) at 50% substitution of $CaF_2$ as observed by X-ray diffraction of post-corrosion surface reaction films.

Figure 7:
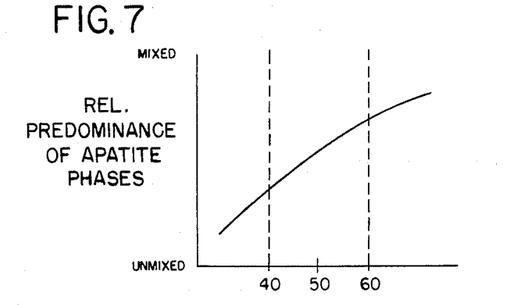
FIG. 7 is a graph showing the relationship between the relative predominance of apatite phases (unmixed to mixed along the y coordinate) and molar % substitution of CaO with $CaF_2$ (the x coordinate) for 52S4.6 glass.

As shown by FIG. 7, the presence of critical concentrations of $CaF_2$ in the glass enhances the formation of mixed apatites in the reactive surface layer as well. As mentioned above, natural bone mineral has been shown to be a mixed carbonate apatite, thereby emphasizing the importance of this aspect of the mineralization process. This experimental work has as its basis X-ray diffraction analysis which demonstrates a change in the relative intensity of the (210)/(002) and (211)/(002) X-ray peaks with increasing $CaF_2$ substitution. The carbonate or hydroxyl apatite (210)/(002) peak ratios more closely correspond to the 0% and 25% $CaF_2$ substitution whereas the 50% $CaF_2$ substitution corresponds more closely with the peak ratios for mixed carbonate-hydroxl-fluoroapatites with varying proportions of the anionic constituents.

Resistance to demineralization of the 52S4.6 glass increases proportionally to the percent substitution of $CaF_2$ for CaO, reaching a plateau at approximately 60-70% (FIG. 8). These results are based on in-vitro exposure of glass with various levels of $CaF_2$ substitution to a standard 20% formic acid, 10% formaldehyde demineralization solution FIGS. 5-8 graphically depict that the optimal $CaF_2$ substitution for CaO is in the range of 40-60% for the 52S4.6 compositions. The glass remains bioactive while also exhibiting enhanced resistance to demineralization. Further, glass within this optimal range shows enhanced crystallization and a predominance of mixed carbonate-hydroxyl-fluroapatites in the surface reaction film, thereby exhibiting a distribution of phases more closely resembling those observed in naturally mineralizing tissues.

The control material for further studies was 45S5 Bioglass TM samples. Compositions designated F, F/2, and F/4 correspond respectively to substitution of 100%, 50%, and 25% CaO by $CaF_2$. All glasses were melted at 1350° in covered Pt crucibles.

Bone bonding and toxicology tests were done on the control and F/2 glass by the standard methods already described. [J. Wilson, G. H. Pigott, F. J. Schoen and L. L. Hench, "Toxicology and Biocompatibility of Bioglass," J. Biomed. Materas. Res., 15 (1981) 805-817.]

In-vitro surface analysis was done with Fourier Transform Infrared Reflection Spectroscopy after 14 days, 37° C. reaction in tris buffer and after 7 days, 25° C. reaction in the decalcifying fuid used to process the implants and tissues from the in-vivo studies. The resistance of the samples to demineralization was determined by measuring weight change and change in dimensions and/or particle size remaining after decalcification. X-ray diffraction, SEM-EDS, XPS, and AES were used to determine extent of crystallinity and film composition.

Subcutaneous implantation of bulk 45S5 and F/2 Bioglass TM implants in rats and intratibial implantations in rats showed no toxicological effects at 6 and 8 weeks. Thirty-day bone-bonding tests using the mini-pushout test [T. Fujiu and M. Ogino, "Differences in Bonding Behavior with Bone Among Surface Active Glasses and Sintered Apatite," submitted to J. B. M. R., 1983.] showed no difference in bonding ability between the control and the F/2 Bioglass TM implant. Previous histological studies of 6-month and 2-year baboon implants of the F/2 composition also showed bonding and absence of toxicity.

In-vitro tests show, by FTIRRS peak area ratios, that the extent of apatite in the surface film decreases with fluoride addition, but only up to the F/2 level. In contrast, the resistance to demineralization progressively increases as the fluoride content increases. However, spectral analysis of the material left after the decalcification treatment shows considerable difference between the F and F/2 formulas indicating important chemical and structural differences between the two. Surface analysis also indicates that there is less crystalline apatite on the treated surfaces of the high fluoride glasses than on those with low fluoride. Combining these film formation characteristics leads to a surface performance index which defines an optional glass composition.

A disk of Bioglass TM 45S5, in which half of the CaO (approximately 13 mole %) was replaced with $CaF_2$, was subcutaneously implanted in a rat for eight weeks. The absence of any inflammation or discoloration in the surrounding tissue clearly illustrated the nontoxicity of the implant.

A dental device of the same composition was implanted for two years in a baboon root socket. The presence of mature, healthy bone immediately adjacent to the implant, and the lack of any fibrous encapsulation demonstrated the bone-bonding ability of fluoride glass in-vivo. To provide a systematic approach, a series of fluoride substitutions based on the 4565 base composition was selected for in-vitro testing. Samples from each composition were evaluated under a modified MCC-1 static leach test for periods of 1, 3, 7 and 14 days at 37° C. in a tris buffer with an SA/U ratio of 0.1 $cm^{-1}$. Leached surfaces were then examined by FTIR reflection spectroscopy and X-ray diffraction, and solution analysis performed by ICP.

Figure 9:
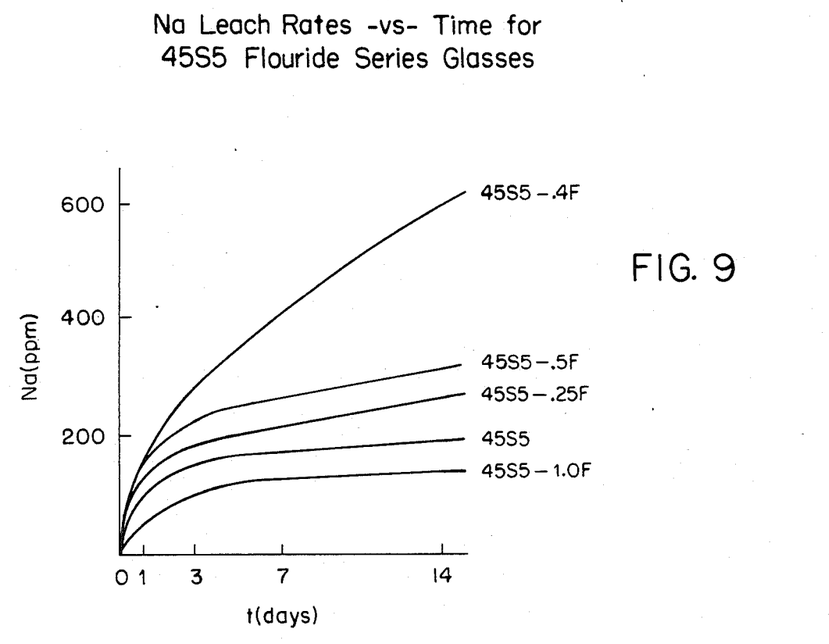
FIG. 9 is a graph showing Na leach rates vs. time for 45S5 fluoride series glasses.

In FIG. 9, solution concentrations of Na are plotted as a function of corrosion time over the range of fluoride substitution. Na leach rates are seen to increase for all intermediate substitutions relative to both the fully substituted and base compositions.

Figure 10:
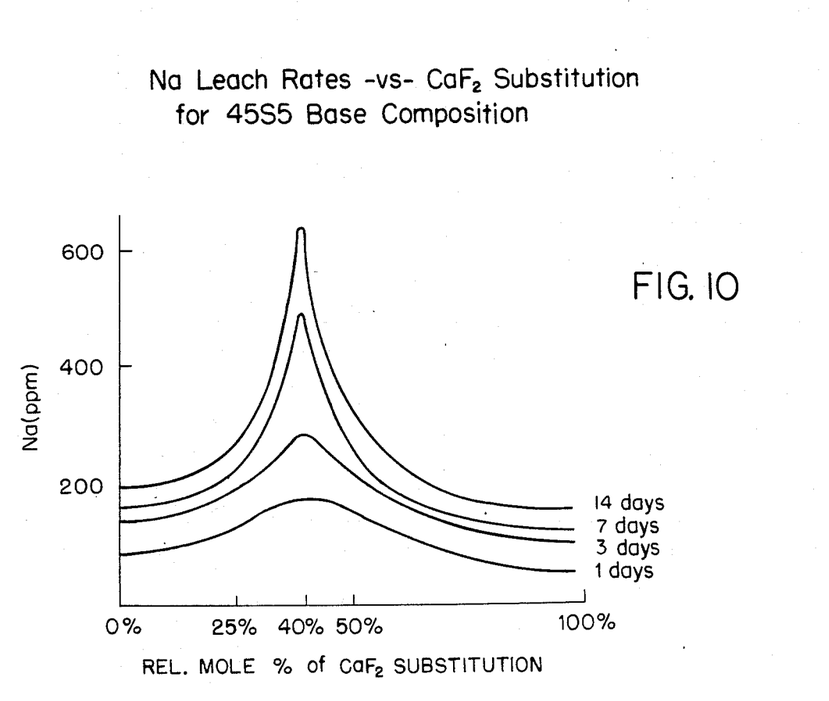
FIG. 10 shows Na leach rates vs. $CaF_2$ content for various time periods.

FIG. 10 shows Na concentration vs. fluoride content for successive time periods, and a sharp increase in the Na leach rate for the 40% substitution is shown beginning at 7 days and increasing further by 14 days. Si data shows qualitatively the same result as do Ca and pH results, though not as dramatically in the latter two cases. The unexpected range of leach rate variability in the intermediate compositions suggests that no single mechanism dominates leaching behavior over the full range of substitution; but rather that several simultaneous mechanisms combine to produce a particular effect at a given composition.

Figure 11:
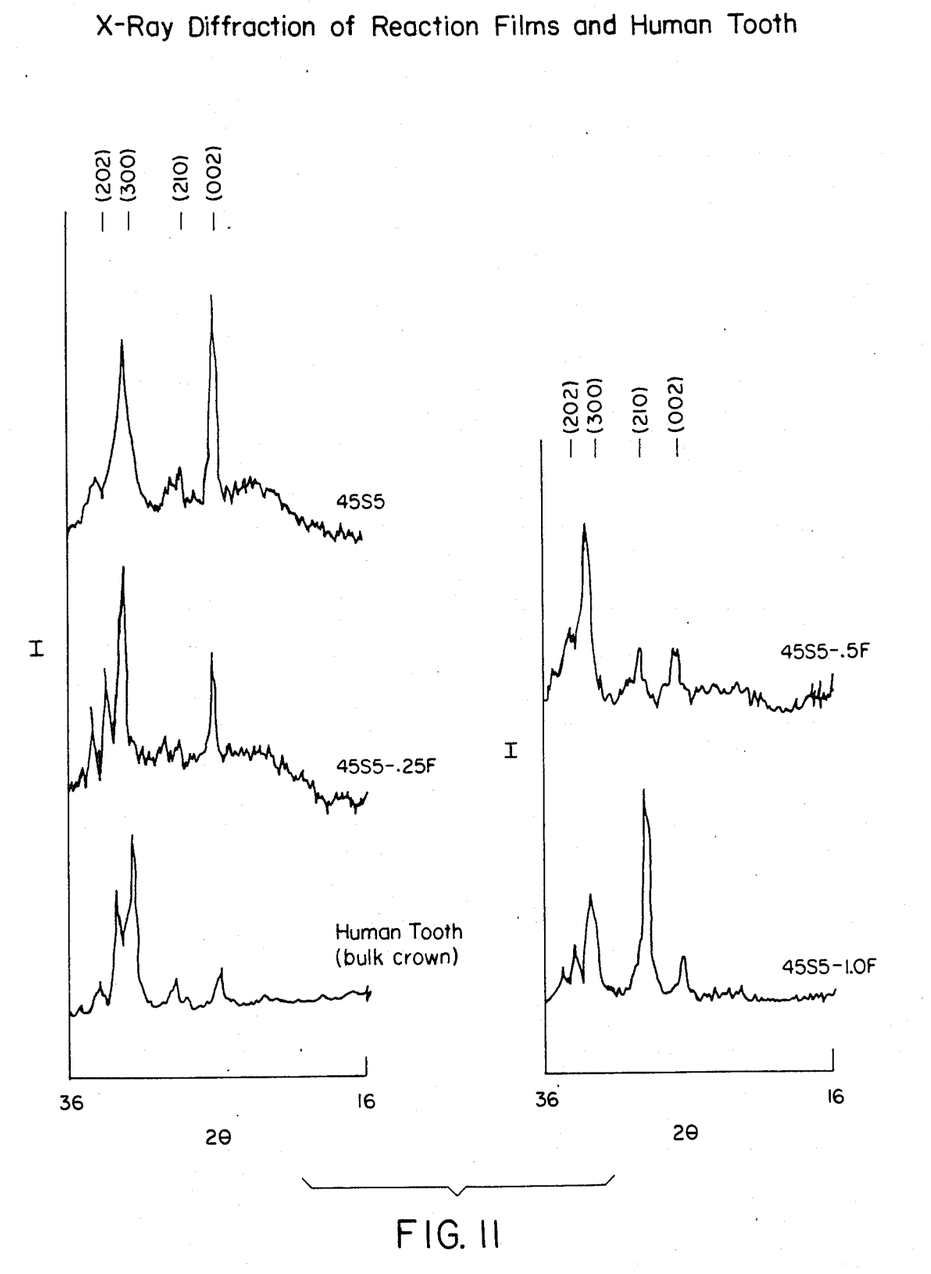
FIG. 11 shows X-ray diffraction patterns of reaction films and human tooth.

An examination of X-ray diffraction patterns from 14-day samples is presented in FIG. 11. Moving from top to bottom, the loss of amorphous baseline and improvement in peak resolution indicate an increasingly crystalline nature in the apatite reaction layer with greater fluoride substitution. If changes in the relative intensities of diffracting planes are examined, a definitive shift from the (002) plane in the base composition to the (210) plane in the fully substituted glass is seen. It is important to note that a pattern from human tooth appears to fit into the series in the middle of this transition, somewhere between the 25% and 50% substitution.

Figure 12:
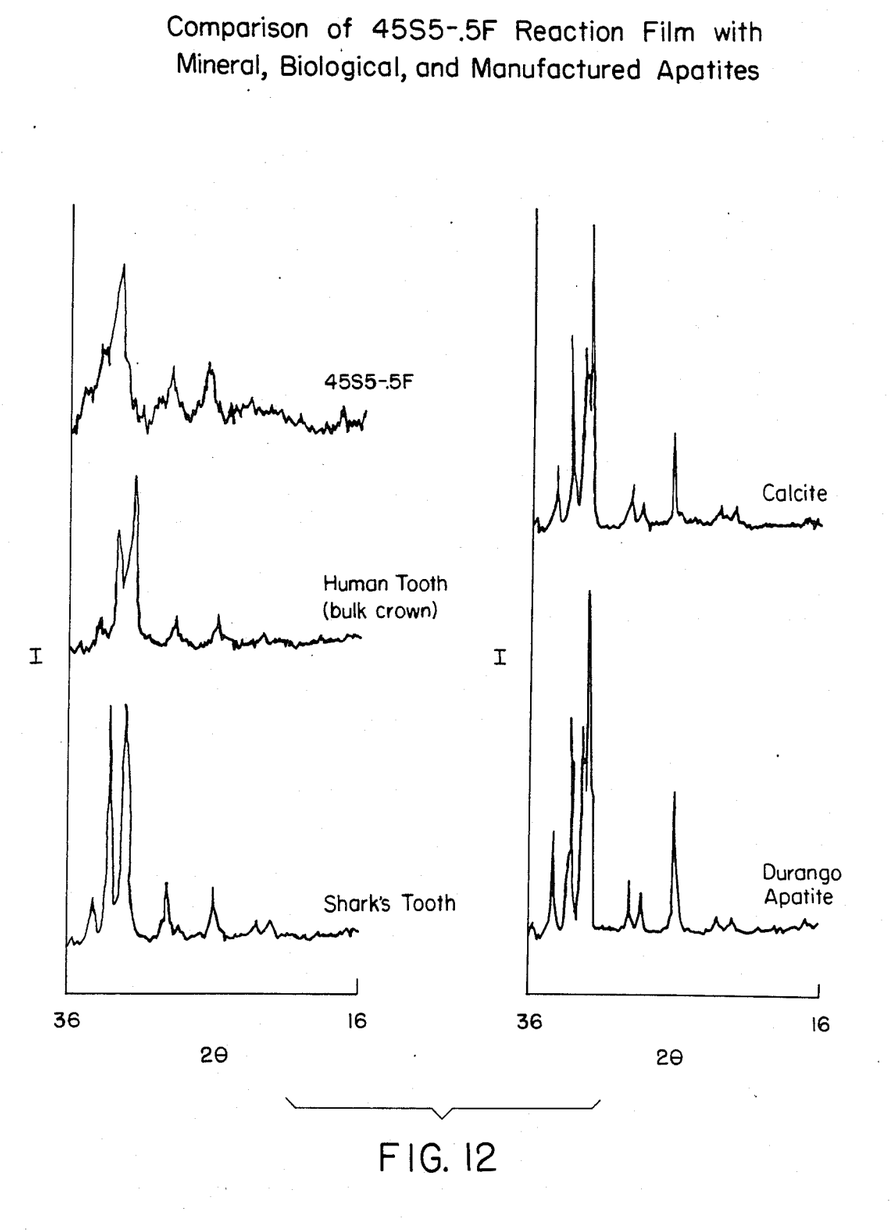
FIG. 12 shows a comparison of a 45S5 glass with substitution of 50% CaO by $CaF_2$ (45S5-.5F) with various mineral, biological and commercial apatites.

A comparison of the 50% substitution at 14 days with various biological, mineral and commercial apatites is shown in FIG. 12. It can be seen that the apatite reaction layer on the Bioglass TM bears a striking resemblance, both in terms of peak positions and relative intensities, to the naturally occurring biological forms in human and shark teeth. Similarly, Calcitite ® matches very closely with the naturally occurring mineral form in Durango apatite. A comparison of the ratio of relative intensity between the (002) and (210) planes for 14-day samples and various JCPDS standards for mixed and pure apatite forms suggests that increasing fluoride content results in the formation of a more "mixed" form of apatite in the reaction layer exhibiting a greater degree of Na, F and $CO_3$ substitution. Other investigators have noted that the composition of bone mineral is more similar to that of the "mixed" forms of apatite.

Figure 13:
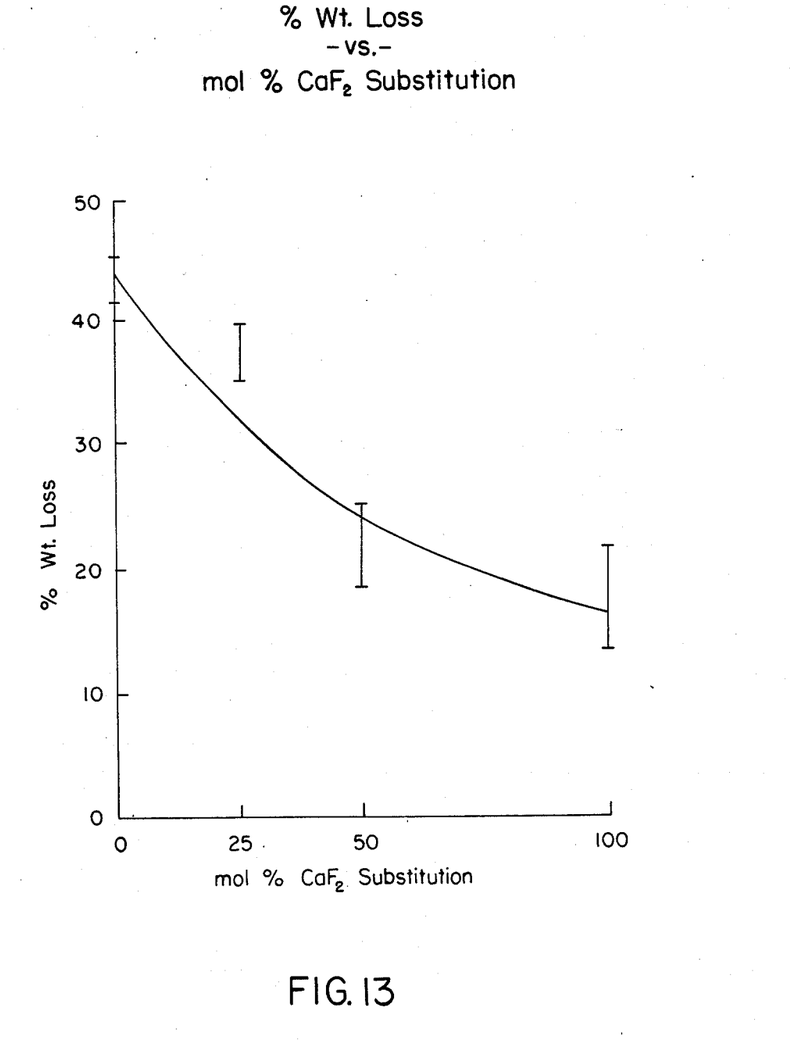
FIG. 13 shows percent weight loss plotted as a function of mole percent $CaF_2$ substitution.

One of the unexpected observations on the effects of fluoride in Bioglass ™ 45S5 was made in the preparation of tissue-implant sections for histological examination. It was noted that implants containing fluoride were much more difficult to section because standard decalcifying treatments failed to sufficiently "soften" the glass. This led to an experiment where a sample of each substitution level was treated in a solution of 20% formic acid and 10% formaldehyde for 7 days at room temperature. The results are presented in FIG. 13 where % weight loss is plotted as a function of fluoride content. As can be seen, the incorporation of fluoride substantially enhances the resistance of the glass to demineralization.

Figure 14:
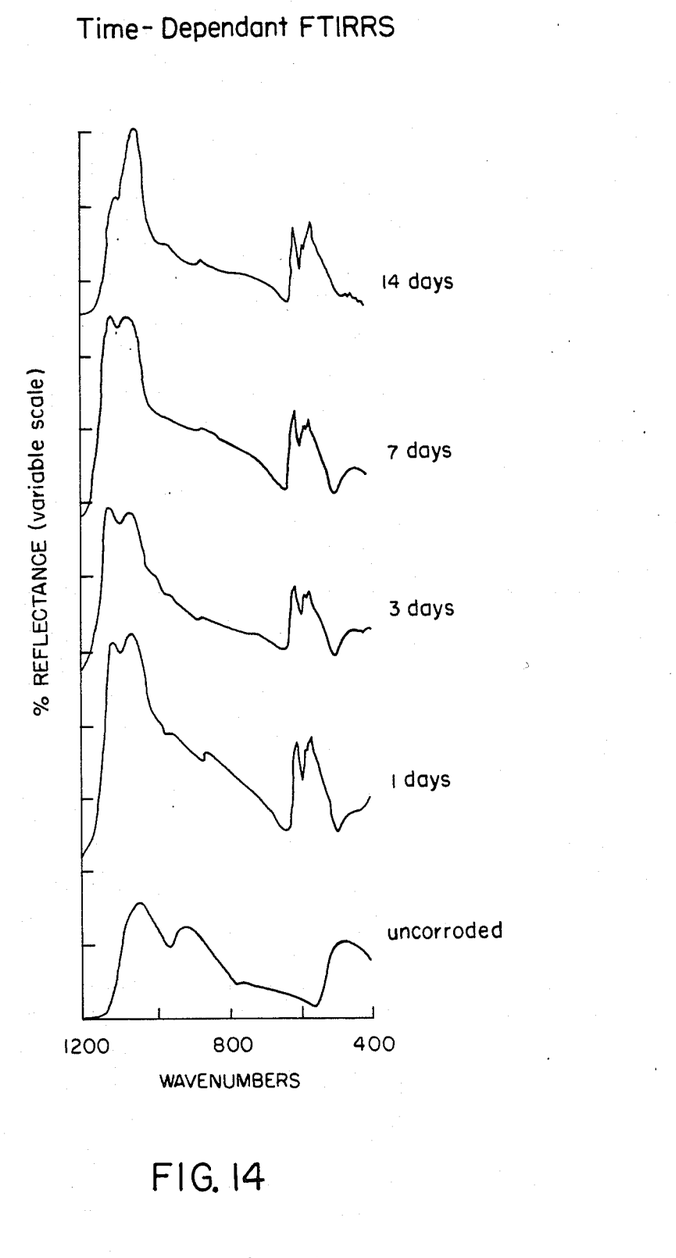
FIG. 14 shows a time-dependent FTIR reflection spectra for a 45S5 glass with substitution of 25% CaO by $CaF_2$
Figure 15:
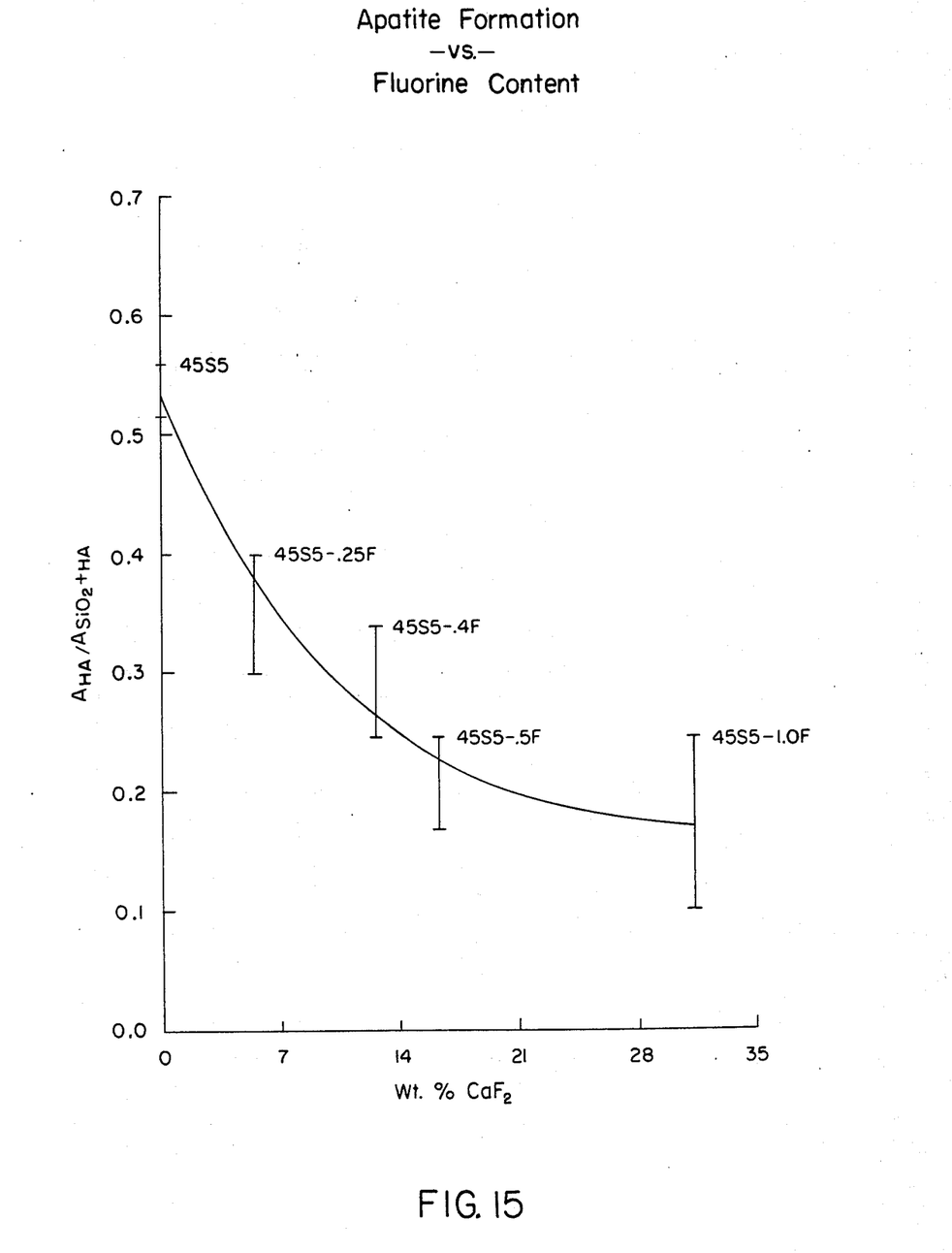
FIG. 15 shows a plot of apatite formation vs. fluorine content.

FIG. 14 shows a time-dependent sequence of FTIR reflection spectra for a 25% substituted fluoride bioglass in-vitro. In the uncorroded condition the SiO bridging and non-bridging stretching vibrations can be seen at 1050 and 930 cm$^{-1}$, and an Si-O bending peak at 460 cm$^{-1}$. By one day, however, $Po_4^{-3}$ stretching vibrations at 1080, 1040 and 960 from the apatite structure dominate the spectrum from 900–1200 cm$^{-1}$ and $PO_4^3$ bending modes are prominate at 600 and 570 cm$^{-1}$. Up until 7 days there is little change in the spectra apart from some slight shifts in relative intensity of the $PO_4^3$ stretching modes. By 14 days, the 1040 band has become dominant. The only discernable feature remaining from the uncorroded glass at one day is the Si-O bending mode at 460 which is reduced at 3 and 7 days, and disappears almost entirely by 14 days. The problems in quantifying apatite formation from the FTIR spectra are two-fold: the variability of reflected intensity with surface finish, and the overlapping of apatite and Bioglass ™ bands precludes any direct comparison of peak areas and relative intensities between spectra. To alleviate this problem, the ratio of peak areas from 960–1150 cm$^{-1}$ (containing both $PO_4^{-3}$ and Si-O modes) to peak areas from 530–630 cm$^{-1}$ (containing only $PO_4^{-3}$ modes) was calculated for each of the 14-day samples. These ratios were then compared as a function of fluoride substitution. The result, shown in FIG. 15, demonstrates that the addition of fluoride acts to reduce the amount of apatite formation, substantially at first, and more gradually by 50% substitution.

Figure 16:
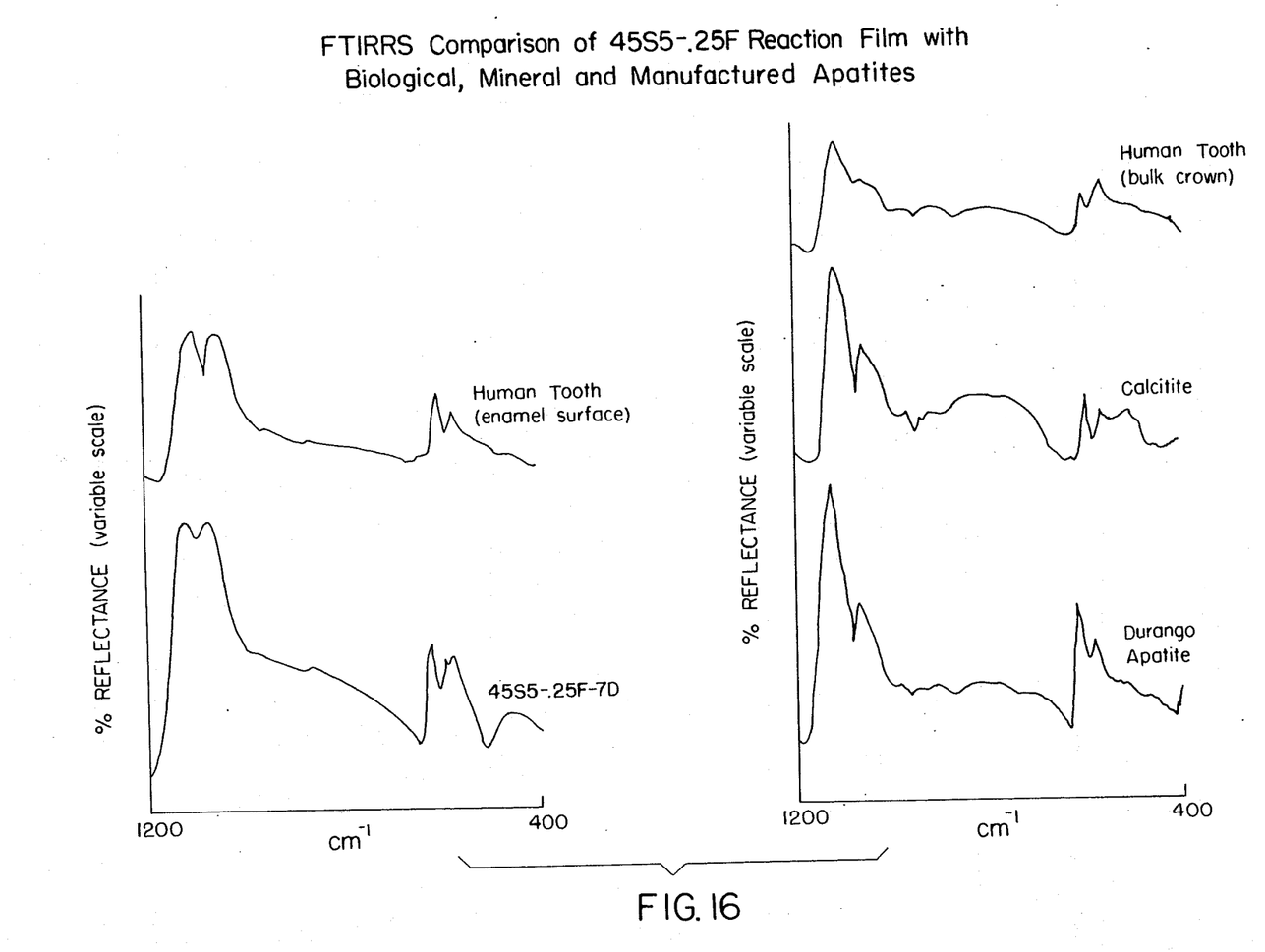
FIG. 16 shows a comparison of a 45S5 glass with substitution of 25% CaO by $CaF_2$ (45S5-.25F) with various mineral, biological and commercial apatites.

In FIG. 16, a comparison of the 25% substitution at seven days with various biological, mineral, and commercial apatites is seen. Looking first at the spectra from human tooth, clear evidence of structural distinctions between the enamel surface and the bulk crown or dentin is seen. It is interesting to note that, qualitatively, the spectrum of the fluoride-Bioglass ™ reaction layer bears a strong resemblance to that of human enamel, while Calcitite ® shares spectral similarities with human dentin and Durango apatite.

Figure 17:
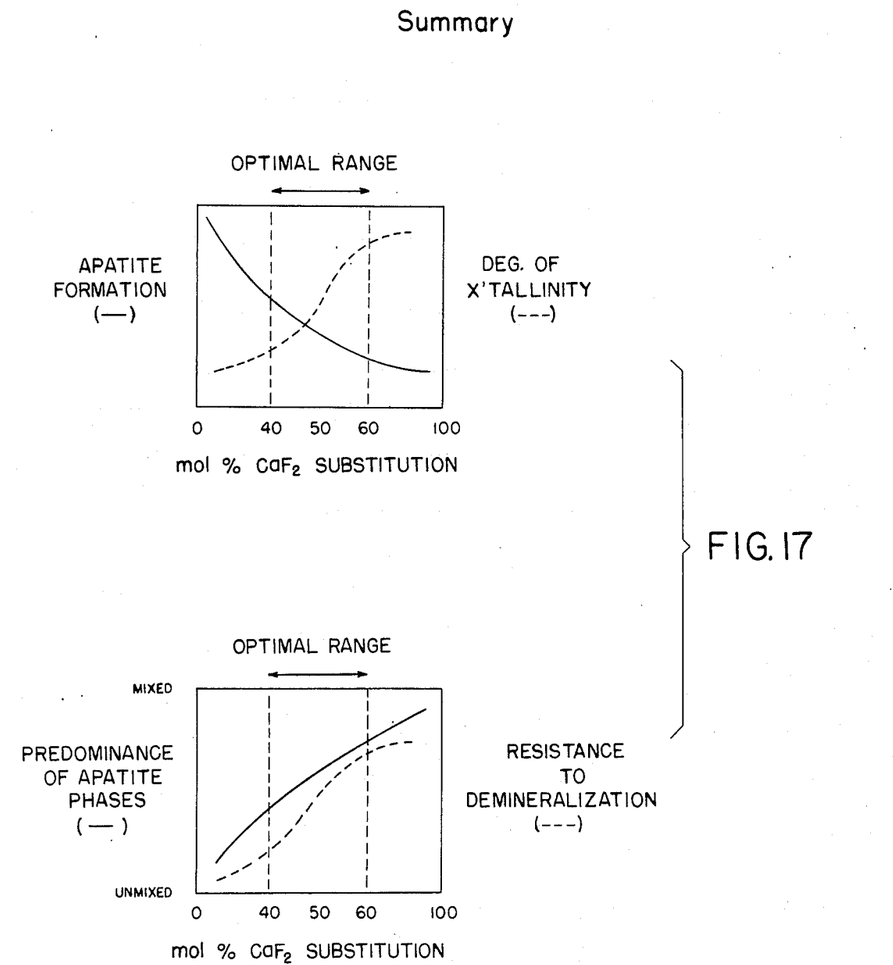
FIG. 17 shows a qualitative, graphical summary of the effect of fluoride in four performance areas (apatite formation, degree of crystallinity, predominance of apatite phases and resistance to demineralization).

In summary, a qualitative, graphical depiction is shown in FIG. 17 of the effect of fluoride in four performance areas believed to be central to the bonding ability and longevity of controlled surface-active impants in-vivo. First, the relative extent of apatite formation, which declines with increasing fluoride content yet, as shown in the baboon model, forms sufficient apatite for bone-bonding at 50% substitution. Secondly, the relative extent of crystallinity of the apatite layer which forms - observed to increase with greater fluoride content which may explain the apparent equivalence in bonding ability between low-fluoride glasses with more, less-crystalline apatite, and higher fluoride glasses with less, more-crystalline apatite. Thirdly, the promotion of a more "mixed" type of apatite structure with greater similarlity to natural biological forms observed -to increase with greater fluoride substitution. And, finally, a substantially increased resistance to demineralization seen with greater fluoride content. A combination of these performance indices suggests that an optimum range of 30–50% would be useful for dental applications where successful bonding combined with biocompatibility and increased resistance to longterm demineralization is desirable.

Having now fully described the invention, it will be apparent to one with ordinary skill in the art that many changes and modifications can be made thereto without departing from the spirit and scope of the invention as set forth herein.

What is claimed is:

1. A prosthetic device comprising a bioactive glass having the composition of 46.1% $SiO_2$, 2.6% $P_2O_5$, 26.9% CaO and 24.4% $Na_2O$, said percentages being molar percentages, and further characterized by having about 40 molar percent of the CaO substituted by $CaF_2$.

2. The prosthetic device of claim 1 wherein said device is a bulk implant consisting essentially of said bioactive glass.

3. The prosthetic device of claim 1 wherein said device is a prosthetic device coated with said bioactive glass.

4. A method for producing a prosthetic device comprising forming said device from a bioactive glass having the composition 46.1% $SiO_2$, 2.6% $P_2O_5$, 26.9% CaO and 24.4% $Na_2O$, said percentages being molar percentages, and further characterized by having about 40 percent of the CaO substituted by $CaF_2$.

5. The method for producing a prostehtic device wherein said device is a bulk implant device comprising said bioactive glass of claim 4.

6. The method for producing a prosthetic device wherein said device comprises a coating of said bioactive glass of claim 4.

7. A bioactive glass having the composition 46.1% $SiO_2$, 2.6% $P_2O_5$, 26.9% CaO and 24.4% $Na_2O$, said percentages being molar percentages, and further characterized by having about 40 molar percent of the CaO substituted by $CaF_2$.

* * * * *